United States Patent
Decor et al.

(10) Patent No.: US 6,331,434 B1
(45) Date of Patent: Dec. 18, 2001

(54) NITROGEN-CONTAINING SILICONE USEFUL FOR COMPACTING NUCLEIC ACID SEQUENCES AND USE FOR TRANSFORMING CELLS

(75) Inventors: Rachel Decor; Charles Mioskowski, both of Strasbourg; Marc Schmutz, Dingsheim; Alain Wagner, Strasbourg, all of (FR)

(73) Assignee: Aventis CropScience SA, Lyons (FR)

( * ) Notice: Subject to any disclaimer, the term of this patent is extended or adjusted under 35 U.S.C. 154(b) by 0 days.

(21) Appl. No.: 09/521,822

(22) Filed: Mar. 9, 2000

Related U.S. Application Data

(63) Continuation of application No. 09/286,406, filed on Apr. 5, 1999, now Pat. No. 6,068,980.

(30) Foreign Application Priority Data

Apr. 6, 1998 (FR) .................................................. 98 04510

(51) Int. Cl.[7] .................................................. C12N 15/88
(52) U.S. Cl. .......................... 435/458; 435/459; 435/470; 435/471
(58) Field of Search ................................ 435/6, 458, 459, 435/470, 471, 440

(56) References Cited

U.S. PATENT DOCUMENTS 5,302,523   4/1994   Coffee et al. .

FOREIGN PATENT DOCUMENTS 0572907    12/1993   (EP) .
WO9706833   2/1997   (WO) .

OTHER PUBLICATIONS

Fang et al. (1998) Nucleic Acids Research 26:588.
From et al. (1990) Bio/Technology 8:833.

*Primary Examiner*—James Ketter
(74) *Attorney, Agent, or Firm*—Baker Botts L.L.P.

(57) ABSTRACT

The present invention relates to a method of transforming cells in which an appropriate quantity of nucleic acid fragments is introduced into the cells. The nucleic acid fragments are introduced in the form of a nucleic acid composition comprising a nitrogen-containing silicone, useful for compacting the nucleic acid fragments; the compositions comprise aggregates of nucleic acid fragments and silicones according to the invention.

6 Claims, No Drawings

NITROGEN-CONTAINING SILICONE USEFUL FOR COMPACTING NUCLEIC ACID SEQUENCES AND USE FOR TRANSFORMING CELLS

"This is a continuation of application Ser. No. 09/286,406 filed Apr. 5, 1999." Now U.S. Pat. No. 6,068,980.

The present invention relates to a method of transforming cells in which an appropriate quantity of nucleic acid fragments is introduced into the cells. The nucleic acid fragments are introduced in the form of a nucleic acid composition which comprises, in an appropriate vehicle, at least one nucleic acid fragment and at least one compacting agent comprising a nitrogen-containing silicone, useful for compacting the nucleic acid fragments; the compositions comprise aggregates of nucleic acid fragments and silicones according to the invention, To transform cells by genetic engineering by introducing a nucleic acid fragment foreign to the said cell (or heterologous) by transfection, it is necessary, beforehand, to compact the nucleic acid fragments. This compacting is carried out by means of hyperbranched polyamine compounds such as spermine or polyethylenimines (Garcia Ramirez et al., *Biopolymers*, vol. 34, 1984, pp. 285–292; WO 97 06833). It is also known to use monomers of silanes to condense DNA for the purpose of its structural study without, however, seeking to transform cells (Fang Y. and Hoh J: "Surface-directed DNA condensation in the absence of soluble multivalent cations" *Nucleic acids Research*, vol. 26, No. 2, Jan. 15, 1998, pages 588–593).

It is however necessary to find new compacting agents so as to obtain good protection of the nucleic acids and to make it possible to vary the media used for the transfection of cells depending on the applications. The present invention provides a solution to this problem.

The present invention relates to a method of transforming cells in which an appropriate quantity of nucleic acid fragments is introduced into the cells, characterized in that the nucleic acid fragments are introduced in the form of a nucleic acid composition which comprises, in an appropriate vehicle, at least one nucleic acid fragment and at least one compacting agent comprising a nitrogen-containing silicone.

According to the present invention, "nucleic acid fragment" is understood to mean a nucleotide sequence which may be of the DNA or RNA type, preferably of the DNA, in particular double-stranded, type.

Nitrogen-containing silicone is understood to mean according to the invention any compound comprising in its structure at least one silicon atom on which at least one nitrogen-containing hydrocarbon radical comprising at least one nitrogen atom is grafted.

The structure of the nitrogen-containing silicone according to the invention is an oligomer. Oligomer is understood to mean a chain of monomers of at least 2 silanes and less than 30 silanes, advantageously comprising 3 to 20 silanes.

The nitrogen atom in the hydrocarbon radical according to the invention is in the form of a primary, secondary or tertiary amine, preferably a primary amine, optionally in the form of an ammonium salt, or alternatively in the form of functions of the guanidine or amidine type.

Advantageously, the nitrogen-containing hydrocarbon radical according to the invention is an atine-containing hydrocarbon radical comprising at least one amine function as defined above, preferably at least one primary amine function (–NH$_2$).

Hydrocarbon radical is understood to mean according to the invention any radical essentially consisting of carbon and hydrogen atoms, the hydrogens being optionally partly or completely replaced by halogens, and optionally comprising oxygen, nitrogen, sulphur or phosphorus atoms.

Preferably, the hydrocarbon radical is chosen from the alkyl, cycloalkyl and aryl radicals and the polycyclic radicals comprising several aliphatic and/or aromatic rings.

Alkyl radical is understood to mean according to the invention preferably any saturated or unsaturated, linear or branched alkyl radical which is optionally interrupted by one or more oxygen atoms, and in the case of several oxygen atoms the latter are not adjacent, which is optionally interrupted by one or more secondary or tertiary amine, carbonyl, carbonyloxy or oxycarbonyl, carbonate, carbamate or urea functions and the likce, which is optionally sustituted with one or more groups chosen from halogens, hydroxyl or primary, secondary or tertiary amine, or cycloalkyl, aryl or polycyclic radicals. Advantageously, the alkyl radical according to the invention comprises from 1 to 10 carbon atoms, preferably at least three carbon atoms, more preferably from 3 to 5 carbon atoms. Advantageously, the alkyl radical is chosen from methyl, ethyl, propyl, isopropyl, butyl, isobutyl, tert-butyl and pentyl radicals and the various isomers of pentyl This definition of alkyl radicals also applies to the cycloalkyl radicals according to the invention, it being understood that the rings comprise at least three elements, comprising in particular the cyclopropyl, cyclopentyl, cyclobutyl or cyclohexyl radicals, as well as monosaccharides, in particular pentoses or hexoses such as the derivatives of glucose.

Aryl radical is understood to mean according to the invention any aryl or heteroaryl radical, optionally substituted with one or more radicals chosen from the alkyl, cycloalkyl or polycyclic radicals and/or with one or more groups chosen from halogens, hydroxyl or primary, secondary or tertiary amine.

Preferably, the amine-containing hydrocarbon radical according to the invention is chosen from the 3-aminopropyl or 3-(2-aminoethylamino)propyl radicals.

Among the amine-containing silicones according to the invention are the organic silicones or the derivatives of silica.

The organic silicones according to the invention comprise at least one silicone unit which follows:

in which,

R1 is a nitrogen-containing hydrocarbon radical as defined above,

R2 represents the R1 radical, a hydroxyl radical or a hydrocarbon radical,

R3 represents R2 or the radical of formula

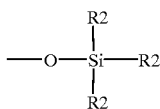

in which R2 is defined above, x and y, which are identical or different, are 0, 1 or 2, it being understood that the sum x+y is less than or equal to 3.

According to a specific embodiment of the invention, the amine-containing silicone is chosen from the silicones of general formula I or II which follow:

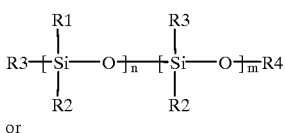

(I)

or

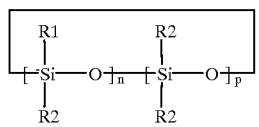

(II)

in which,

R1, R2 and R3 are defined above,

R4 represents a hydrogen atom, a hydrocarbon radical or a radical of formula

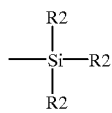

in which R2 is defined above, n is at least equal to 1, m is greater than or equal to 0 and p is greater than or equal to 0, on the condition that the sum n+p is greater than or equal to 3.

Preferably, n is between 1 and 10, more preferably between 5 and 9, and m or p are between 0 and 9.

According to a specific embodiment of the invention, in the silicones of general formula I, R2 represents a hydroxyl radical or a hydrocarbon, in particular alkyl, radical, R3 represents a hydroxyl radical and R4 represents a hydrogen atom, n is between 7 and 9 and m is equal to 0.

The silicones according to the invention are prepared according to the customary methods of the state of the art, which are described in particular in *Organic Chemistry* (vol. 29, Polymer synthese, vol. I, chap. 4, pp. 114–139), by Patai and Rappopor (The chemistry of Silicon Compound, Part 2, pp. 1291–1357), Desachler et al. (Angew. Chem., Int. Ed. Engl., 25, 1986, 236), and in Patent Application JP 9 100 353.

When the amine-containing silicone is a silica derivative, it is advantageously according to the invention a silica support, in the form of particles which are grafted with at least one nitrogen-containing hydrocarbon radical as defined above, Preferably, the particles of silica are nanoparticles having a mean diameter of between 10 and 100 nm, preferably of between 30 and 60 nm, having a specific surface area of about 90 to 100 m$^2$/g. The silica support may be a layer of silica which coats a metallic support; it is advantageously according to the invention a tungsten or gold support. The support is advantageously a particle having a diameter ranging from about 0.5 to 2 $\mu$m, preferably of about 1 $\mu$m.

The mean diameter of the particles is defined by size and measured by diffraction of light or by visualization under a transmission electron microscope. The measuremnent of the specific surface area is carried out by the BET absorption isotherm.

The particles according to the invention are preferably prepared according to the so-called "Stöber" method by condensation of tetraethoxysilane in ammoniacal aqueous alcoholic medium, followed by a distillation at constant volume of the ammonia and of the alcohol. The water into which the silica particles were transferred is removed by azeotropic distillation in the presence of toluene, followed by heating under vacuum which makes it possible to remove the hydration layers at the surface of the silica.

This type of preparation makes it possible to obtain well equilibrated particles (low dispersity of the diameters), free of macro- or micropores (the attaching operations take place exclusively at the surface) and free of contaminations (in particular absence of the salts which are found in precipitated silica).

The silica particles or the layers of silica coating a metallic support are then functionalized by grafting silanes comprising at least one nitrogen-containing hydrocarbon radical described above, in particular covalently.

Many procedures describe the use of alkoxysilanes or of chlorosilanes for functionalizing silica surfaces either in the form of a prehydrolysed mixture or, if the reaction does not take place in a medium which is at least partially aqueous, by reacting with the water in the surface hydration layers.

Another synthesis route described in the literature (Shoji Hara, Akira Dabashi Journal of Chromatography, 186 (1979) 543–552) consists in reacting, in a rigorously anhydrous medium, an alkoxysilane with the surface siloxanes of the nanoparticles previously freed of any adsorbed water. The reaction is carried out for 12 h in toluene at 100° C. and the alcohol formed (ethanol) is removed by azeotropic distillation. The silica is filtered and rinsed with various solvents so as to remove therefrom the excess siloxanes which did not become attached.

Preferably, the functionalization is carried out according to this second type of preparation. The functionalization of the silica may be carried out with various types of alkoxysilanes, preferably with a silane of the following formula:

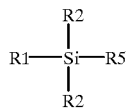

in which R1 and R2 are defined above and R5 represents an alkoxy radical.

Preferably, R5 represents a methoxy, ethoxy, isopropyloxy, chloride or acetoxy radical.

This functionalization may be carried out in the presence of other silanes for which R1 and/or R2 and/or R5 are different, so as to vary the nitrogen-containing hydrocarbon radical content of the particles obtained. In this case, if nSi—OH is the number of mols of surface silanols and ni the respective number of mole of the various functionalities i added, the reaction is carried out such that:

This mode of preparation makes it possible to control the relative quantity of each function at the surface of the nanoparticles of silica such that for ki, the rate constant for condensation of the compound i, the final molar percentage of a compound 1 at the surface of the nanoparticles will be close to klnl/Skini.

Advantageously, the molar ratio (nitrogen atoms of the nitrogen-containing silicone compound)/(phosphate functions of the nucleic acid fragment) is between 0.1 and 6000, preferably between 1 and 1000.

The appropriate vehicle is an aqueous vehicle, preferably an aqueous solution, which is customary as compacting medium for nucleic acid fragments. It may also comprise additives such as buffers or salts, provided that they do not degrade the nucleic acid fragments and/or destroy the aggregates obtained.

It was observed that the compositions according to the invention exhibited enhanced stability of the DNA fragments, in particular by enhancing the protection of the said fragments against enzymatic degradations, in particular by DNAses.

The present invention also relates to the use of the silicone compounds (organic silicones or silica derivatives) as defined above, for compacting and protecting nucleic acid fragments, in particular for protecting against enzymatic degradations, more especially by DNAses.

The transformation of cells may be carried out by any method known in the state of the art (in particular Jean-Yves Legendre et al., *medecine/sciences*, 1996; 12; 1334–41), The cells transformed by the method according to the invention may be animal, plant, bacterial, fungal or yeast cells.

For animal cells, they may be any cell of animal origin, in particular from mammals, especially of human origin, but also insect cells.

For the plant cells, they will be advantageously cells of monocotyledonous or dicotyledonous plants, and more particularly crop plants, intended or otherwise as animal or human food, such as maize, wheat, rapeseed, soya bean, rice, sugar cane, beet, tobacco, cotton and the like. The plant cells transformed may be undifferentiated or differentiated, such as for example protoplast cells or pollen cells. In the latter case, the pollens being rich in DNAses, the transformation will be facilitated by the protection of the nucleic acid fragments by means of the silicone compounds according to the invention.

For the transformation of the plant cells, a series of methods consists in bombarding cells, protoplasts or tissues with particles to which the DNA sequences are fixed. Another series of methods consists in using, as means of transfer into the plant, a chimeric gene inserted into an Agrobacterium tumefaciens Ti or Agrobacterium rhizogenes Ri plasmid.

Other methods may be used, such as microinjection or electroporation or alternatively direct precipitation by means of PEG.

Persons skilled in the art will make the choice of the appropriate method according to the nature of the host organism, in particular of the plant cell or of the plant.

The subject of the present invention is also the plants containing plant cells transformed above, in particular the plants regenerated from the transformed cells. The regeneration is obtained by any appropriate is method which depends on the nature of the species.

For the methods of transforming plant cells and of regenerating plants, there may be mentioned in particular the following patents and patent applications: U.S. Pat. No. 4,459,355, U.S. Pat. No. 4,536,475, U.S. Pat. No. 5,464,763, U.S. Pat. No. 5,177,010, U.S. Pat. No. 5,187,073, EP 267, 159, EP 604 662, EP 672 752, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat No. 5,565,346, U.S. Pat. No. 5,484,956, U.S. Pat. No. 5,508,468, U.S. Pat. No. 5,538,877, U.S. Pat. No. 5,554,798, U.S. Pat No. 5,489,520, U.S. Pat. No. 5,510,318, U.S. Pat. No. 5,204,253, U.S. Pat. No. 5,405,765, EP 442 174, EP 486 233, EP 486 234, EP 539 563, EP 674 725, WO 91/02071 and WO 95/06128.

Other characteristics of the invention will appear on reading the examples below.

EXAMPLE I

Preparation of the functionalized particles of silica

Nanoparticles were functionalized by a mixture of;

3-aminopropyldimethylethoxysilane 10% trimethylethoxysiloxane 90% or octyltrimethoxysilane 1% 3-aminopropyltrimethoxysilane 1% methyltrimethoxysilane 92%.

In this example, the mixtures are produced as far as possible with the same type of reactive alkoxysilane functions (only monomnethoxy or triethoxy and the like) in order to minimize differences in reactivity.

Procedure:

The nanoparticles, once dried, are handled in flame-sterilizeed glassware, under an inert argon atmosphere. All the organic solvents used are continuously distilled or dried according to the customary methods.

The nanoparticles of silica are suspended by means of ultrasound in toluene in a two-necked flask equipped with a septum, a condenser and under an argon pressure. The alkoxysilane is added in excess using a syringe ($2.5 \times 10^{-3}$ mol/g dry $SiO_2$).

For the functionalizations with mixtures of alkoxysilanes, the latter are previously mixed in a round-bottomned flask, under argon, containing toluene, and the whole is added using a canula-like tube over the suspension of nanoparticles.

The reaction medium is homogenized using ultrasound for one to two hours and then heated at the reflux temperature of toluene for a minimum of three hours for the compounds carrying three alkoxysilane functions per atom of silicon or for about 12 hours for the compounds containing only one alkoxysilane function per silicon atom.

The medium is then centrifuged at cold temperature (4800 rpm, 3838 G, 4° C.). The supernatant is removed, the pellet is resuspended in toluene (anhydrous) and then centrifuged. The operation is repeated three times. The final pellet is dried under vacuum (appearance; white powder).

The nanoparticles thus obtained can be suspended in the appropriate solvent (including water) for the desired use or the subsequent functionalization steps.

EXAMPLE II

Compaction and protection of the DNA:

EXAMPLE II.1

Compaction and protection with the functionalized nanoparticles according to the invention The nanoparticles, at least partially functionalized with 3-aminopropylsilanes, are suspended with the aid of ultrasound in water (filtered on a sterilizing filtration membrane) or in a buffer (Hepes, NaCl, PBS) containing no amines, The sample of nanoparticles is added to a solution of DNA.

If the DNA is added to the suspension of nanoparticles, flocculation is observed due to the aggregation of several nanoparticles around the same DNA strand. Such preparations allow enhanced protection of the DNA against the degradations caused by DNAses compared with the state of the art.

EXAMPLE II.2

Compaction with polyaminosiloxanes

Products Used:

oligoiners of 3-aminopropylsilanetriols in aqueous solution at 40% oligomers of N-(2-amrinethyl)-3-aminopropylmethylsilane (oil)

products resulting from the polymerization, in the presence of traces of water, of 3-aminopropyltrimethoxysilane in toluene.

To test the absence of compaction in the presence of the monomers:

3-aminopropyltrimethoxysilane (oil)

3-aminopropylmethyldiethoxysilane (oil)

DNA:

Various plasmids of bacterial origin, supercoiled, of variable length (from 10.2 kb to 3.2 kb) and of various types (Bluescript, Lac-Z, encoding luciferase, β-galactosidase).

2.1 Preparations:

The DNA-polyaminosiloxane complexes were prepared in various media: water (filtered on sterilizing filtration membrane), 75 mM to 150 mM NaCl medium, Hepes buffer medium and $CaCl_2$ medium.

The mixtures were prepared as follows:

The concentrated aqueous solution of polyaminosiloxanes is homogenized using ultrasound. An aliquot of this solution is diluted in half the final volume in buffer and homogenized. The DNA, in solution in the buffer, is added volume for volume to the solution of polyaminosiloxanes. The whole is stirred by means of a vortex. The order of addition of the various components may be modified.

The same procedure was carried out for the control with the monomers which did not give rise to any compaction.

2.2 Effect of Compaction, Protection of the DNA:

During the electron microscopy examination of the mixtures between the DNA and each of the products different figures of compacted DNA are observed, some of which are similar to those obtained in the presence of histones or of known compacting agents such as spermine or polyethylenimines (cf. for example M. Garcia Ramirez, J. A. Subirana, Biopolymers, vol. 34, p. 285–292, 1984).

The figures observed are different in nature depending on the concentration and the product used.

A study of the oligomers of 3-aminopropylsilanetriols clearly showed a dose effect; for increasing (from 0.1 to 6000) (mol of amine function of the polysiloxane)/(mol of phosphate of the DNA) ratios, increasing compaction is observed.

The ethydium bromide (EtBr) exclusion technique made it possible to prove the high capacity of the products to compact DNA.

This compaction makes it possible to protect the DNA from degradations.

EXAMPLE III

Transfection tests were carried out under various conditions and on three types of cell lines (NIH3T3, HeLa and HepG2). Transfection activities are observed.

EXAMPLE of Preparations:

DNA at 10 μg/ml, oligomers of 3-aminopropylailanetriols at $9.1 \times 10^{-7}$ mol/ml (that is to say 30 mols of amines per mol of phosphate).

DNA at 10 μg/ml, oligomers of N-(2-aminoethyl)-3-aminopropylmethylsilane at $3 \times 10^{-8}$ mol/ml (that is to say one equivalent primary amine per phosphate), $9.1 \times 10^{-7}$ mol/ml (30 equivalents primary amines per phosphate) or $3 \times 10^{-5}$ mol/ml (1000 equivalents primary amines per phosphate).

These preparations gave a higher expression than the standard polyamine aggregating agents of the state of the art used at $6 \times 10^{-8}$ mol/ml.

EXAMPLE IV

Transforation of plants

Evaluation of the toxicity is carried out before the trials in vivo. Sixty to seventy mg of cells are transferred into 150-ml flasks containing 10 ml of culture medium and various concentrations of oligomers of N-(2-aminoethyl)-3-aminopropylmethylsilane (0, 1, 2, 4 and 8 mg/l). The cells are collected after 7 days of culture and the fresh weight of the cells is estimated. An increase in the pH (8.1) of the culture medium is observed for concentrations of oligomers of N-(2-aminoethyl)-3-aminopropylmethylsilane of 8 mg/l and inhibition of cell growth is observed, but no toxicity. The molarity of N-(2-aminoethyl)-3-aminopropylmethylsilane for the highest primary amine per phosphate ratio (5333) is 0.16 mM and is equivalent to the polarity of N-(2-aminoethyl)-3-aminopropylmethylsilane in the test of toxicity at 2 mg/l. These results show that the concentrations used for the bombardment are not phytotoxic.

Plant transformation trials were carried out on cells of Arabidopsis (Strain T 87) obtained according to the method described by Axelos (Axelos M. et al., 1992 *Plant Physiol.* 30 (1), 123–128). The technique used is bombardment (Vain Ph et al., 1993 Plant Cell, *Tissue and Organ Culture.*, 33, 237–246). A transient expression as well as a stable expression (production of calli), equivalent to those obtained with spermidine, are observed.

Examples of preparations or bombardment:

Particles of tungsten (Sylvania Chemicals) M17, having a mean diameter of 1 μm, are sterilized in ethanol at 95% in an amount of 1 g/20 ml. Five hundred μl of particles in suspension are collected, washed 3 times in sterile milli Q water and taken up in 500 μl of water final. The precipitation of DNA around the particles is obtained according to the protocol below. The following mixture is prepared by adding in order: 50 μl of M17 particles, 10 μg of DNA, 50 μl of 2.5 M $CaCl_2$, plus N-(2-aminoethyl)-3-aminopropylmethylsilane so as to obtain the primary amine per phosphate ratios of 167; 667; 1333; 2667 and 5333. After 10 minutes, the mixture thus precipitated is used to carry out 2 shots, −10 μg of DNA are mixed with a solution of 2.5 mg of tungsten particles siliconized with 3-aminopropyltrimethoxysilane in 50 μl of water. After 10 minutes, the mixture thus precipitated is used to carry out 2 shots. A transient expression is observed which is substantially equivalent to that for the preceding complex.

What is claimed is:

1. Method of transforming cells in which an appropriate quantity of nucleic acid fragments is introduced into the cells, characterized in that the nucleic acid fragments are introduced in the form of a nucleic acid composition which comprises, in an appropriate vehicle, at least one nucleic acid fragment and at least one compacting agent comprising a nitrogen-containing silicone, wherein the nitrogen-containing silicone comprises at least one silicone unit which follows:

in which:

R1 is a nitrogen-containing hydrocarbon radical,

R2 represents the R1 radical, a hydroxyl radical or a hydrocarbon radical,

R3 represents R2 or the radical of formula

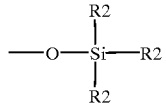

in which R2 is defined above, x and y, which are identical or different are 0, 1 or 2, it being understood that the sum x+y is less than or equal to 3.

2. Method of transforming cells in which an appropriate quantity of nucleic acid fragments is introduced into the cells, characterized in that the nucleic acid fragments are introduced in the form of a nucleic acid composition which comprises, in an appropriate vehicle, at least one nucleic acid fragment and at least one compacting agent comprising a nitrogen-containing silicone, wherein the nitrogen-containing silicone is chosen from the silicones of general formula I or II which follow:

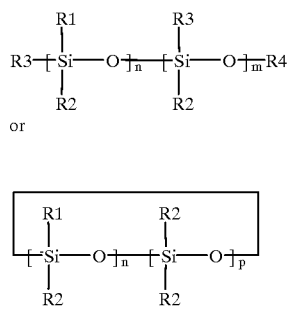

in which,

R1 is a nitrogen-containing hydrocarbon radical,

R2 represents the R1 radical, a hydroxyl radical or a hydrocarbon radical,

R3 represents R2 or the radical of formula

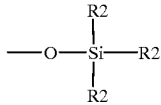

in which R2 is defined above,

R4 represents a hydrogen atom, a hydrocarbon radical or a radical of formula

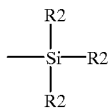

in which R2 is defined above, n is at least equal to 1, m is greater than or equal to 0 and p is greater than or equal to 0, on the condition that the sum n+p is greater than or equal to 3.

3. Method according to claim 2, characterized in that n is between 1 and 10 and m or p are between 0 and 9.

4. Method according to claim 2, characterized in that in the silicones of general formula I, R2 represents a hydroxyl radical or a hydrocarbon radical, R3 represents a hydroxyl radical and R4 represents a hydrogen atom, n is between 7 and 9 and m is equal to 0.

5. Method according to claim 3 wherein n is between 5 and 9.

6. Method according to claim 4 wherein R2 represents an alkyl radical.

* * * * *

UNITED STATES PATENT AND TRADEMARK OFFICE
CERTIFICATE OF CORRECTION

PATENT NO. : 6,331,434 B1
DATED : December 18, 2001
INVENTOR(S) : Decor et al.

It is certified that error appears in the above-identified patent and that said Letters Patent is hereby corrected as shown below:

Column 1,
Line 5, ""This" should read -- This --
Line 6, "1999. Now" should read -- 1999, now --

Column 2,
Line 14, "likce," should read -- like, --; and "sustituted" should read -- substituted --
Line 23, "pentyl" should read -- pentyl. --

Column 3,
Line 16, "which," should read -- which: --
Line 27, "is" should read -- is as --
Line 40, "synthese," should read -- synthesis --
Line 42, "Desachler" should read -- Deschler --
Line 50, "above," should read -- above. --
Line 61, "measuremnent" should read -- measurement --

Column 4,
Line 42, "are" should read -- are as --
Line 54, "nSi—OH>>Sni" should read -- nSi—OH<<Sni --

Column 6,
Line 4, "of;" should read -- of: --
Line 11, "monomnethoxy" should read -- monomethoxy --
Line 15, "sterilizeed" should read -- sterilized --
Line 24, "round-bottomned" should read -- round-bottomed --
Line 26, "canula-like" should read -- cannula-like --
Line 66, "oligoiners" should read -- oligomers --

Column 7,
Line 1, "amrinethyl" should read -- aminoethyl --
Line 56, "aminopropylailanetriols" should read -- aminopropylsilanetriols --

Column 8,
Line 2, "Transforation" should read -- Transformation --
Line 24, "Strain" should read -- strain --
Line 45, "shots," should read -- shots. --

UNITED STATES PATENT AND TRADEMARK OFFICE
CERTIFICATE OF CORRECTION

PATENT NO. : 6,331,434 B1
DATED : December 18, 2001
INVENTOR(S) : Decor et al.

It is certified that error appears in the above-identified patent and that said Letters Patent is hereby corrected as shown below:

Column 9,
Line 40, "which," should read -- which: --

Column 10,
Line 24, "0and" should read -- 0 and --
Line 28, "10" should read -- 10, --
Line 33, "9" should read -- 9, --

Signed and Sealed this

Thirtieth Day of July, 2002

Attest:

Attesting Officer

JAMES E. ROGAN
Director of the United States Patent and Trademark Office